(12) United States Patent
März et al.

(10) Patent No.: US 9,506,909 B2
(45) Date of Patent: Nov. 29, 2016

(54) HOMOARGININE AS A BIOMARKER FOR THE RISK OF MORTALITY

(75) Inventors: Winfried März, Hirschberg (DE); Andreas Meinitzer, Graz (AT); Christiane Drechsler, Würzburg (DE); Stefan Pilz, Graz (AT); Vera Krane, Würzburg (DE); Christoph Wanner, Höchberg (DE)

(73) Assignee: Synlab Medizinisches Versorgungszentrum Heidelberg GmbH, Eppelheim (DE)

( * ) Notice: Subject to any disclaimer, the term of this patent is extended or adjusted under 35 U.S.C. 154(b) by 0 days.

(21) Appl. No.: 13/578,527

(22) PCT Filed: Feb. 10, 2011

(86) PCT No.: PCT/EP2011/051957
§ 371 (c)(1),
(2), (4) Date: Feb. 21, 2013

(87) PCT Pub. No.: WO2011/098519
PCT Pub. Date: Aug. 18, 2011

(65) Prior Publication Data
US 2013/0143240 A1    Jun. 6, 2013

(30) Foreign Application Priority Data
Feb. 12, 2010    (EP) .................... 10153545

(51) Int. Cl.
| G01N 33/50 | (2006.01) |
| A61K 31/198 | (2006.01) |
| G01N 33/68 | (2006.01) |
| A23L 1/305 | (2006.01) |

(52) U.S. Cl.
CPC ............. *G01N 33/50* (2013.01); *A23L 1/3051* (2013.01); *A61K 31/198* (2013.01); *G01N 33/6812* (2013.01); *G01N 2800/32* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| 5,744,305 A | 4/1998 | Fodor et al. | |
| 2004/0081642 A1* | 4/2004 | Loscalzo et al. | 424/94.1 |

FOREIGN PATENT DOCUMENTS

| EP | 0648228 B1 | 4/1995 |
| WO | WO-02/083913 A1 | 10/2002 |
| WO | WO-02/089657 A2 | 11/2002 |
| WO | WO-2006/128419 A1 | 12/2006 |

OTHER PUBLICATIONS

Blackwell et al., European Journal of Clinical Investigation, 37, (2007), p. 364-371.*
Pilz et al., Low Serum Homoarginine is a novel risk factor for fatal strokes in patients undergoing coronary angiography, Stroke, 42, (2011), p. 1132-1134.*
Pilz et al., Associations of homoarginine with bone metabolism and density, muscle strength and mortality: cross-sectional and prospective data from 506 female nursing home patients, Osteoporos Int. 24, (2013), p. 377-381.*
Wever et al., Nitric Oxide Production Is Reduced in Patients with Chronic Renal Failure, Arteriosclerosis, Thrombosis, and Vascular Biology, 19, (1999), p. 1168-1172.*
Marescau et al., Guanidino compounds in serum and urine of nondialyzed patients with chronic renal insufficiency, Metabolism, 46(9), (1997), p. 1024-1031.*
Best et al., The impact of renal insufficiency on clinical outcomes in patients undergoing percutaneous coronary interventions, Journal of Ameircan College of Cardiology, 39(7), (2002), p. 1113-1119.*
Ala-Kopsala et al., "Molecular heterogeneity has a major impact on the measurement of circulating N-terminal fragments of A- and B-type natriuretic peptides," Clin Chem. 50(9):1576-1588 (2004).
Anderson et al., "Molecular basis of human cardiac troponin T isoforms expressed in the developing, adult, and failing heart," Circ Res. 76(4):681-686 (1995).
Bauersachs et al., "Endothelial dysfunction in heart failure," Pharmacol Rep. 60: 119-126 (2008).
Bonow, "New insights into the cardiac natriuretic peptides," Circulation. 93:1946-1950 (1996), retrieved Jan. 29, 2013.
Chen et al., "Role of nitric oxide synthesis in salt-sensitive hypertension in Dahl/Rapp rats," Hypertension. 22:812-818 (1993).
Ferrieres et al., "Human cardiac troponin I: precise identification of antigenic epitopes and prediction of secondary structure," Clin Chem. 44(3):487-493 (1998).
Ford et al., "Explaining the decrease in U.S. deaths from coronary disease, 1980-2000," N Engl J Med. 356(23): 2388-2398 (2007).
Hrabák et al., "Comparison of substrate and inhibitor specificity of arginase and nitric oxide (NO) synthase for arginine analogues and related compounds in murine and rat macrophages," Biochem Biophys Res Commun. 198(1): 206-212 (1994).
Jones et al., "HPLC analysis of asymmetric dimethylarginine, symmetric dimethylarginine, homoarginine and arginine in small plasma volumes using a Gemini-NX column at high pH," J Chromatogr B Analyt Technol Biomed Life Sci. 878(1):8-12 (2010).

(Continued)

*Primary Examiner* — Christine Foster
*Assistant Examiner* — Ellen J Marcsisin
(74) *Attorney, Agent, or Firm* — Clark & Elbing LLP; Kristina Bieker-Brady

(57) ABSTRACT

The present invention relates to the field of laboratory diagnostics. Specifically, means and methods for determining the risk of mortality in a patient based on homoarginine and to reduce the risk of mortality by administration of homoarginine are disclosed. Moreover, the present invention relates to the use of homoarginine for the preparation of a medicament for the treatment of a patient having an increased risk of mortality caused by stroke or a cardiac cause. Furthermore, the present application relates to a pharmaceutical composition comprising homoarginine and a composition for foodstuff supplement comprising homoarginine.

7 Claims, No Drawings

(56) References Cited

OTHER PUBLICATIONS

Karl et al., "Development of a novel, N-Terminal-proBNP (NT-proBNP) assay with a low detection limit," Scand J Clin Lab Invest. 59(Suppl 230):177-181 (1999).
Knowles et al., "Formation of nitric oxide from L-arginine in the central nervous system: a transduction mechanism for stimulation of the soluble guanylate cyclase," Proc Nati Acad Sci USA. 86:5159-5162 (1989).
Lajer et al., "Plasma concentration of asymmetric dimethylarginine (ADMA) predicts cardiovascular morbidity and mortality in type 1 diabetic patients with diabetic nephropathy," Diabetes Care 31(4):747-752 (2008).
März et al., "Homoarginine, cardiovascular risk, and mortality," Circulation. 122:967-975 (2010).
Meinitzer et al., "Reference values for plasma concentrations of asymmetrical dimethylarginine (ADMA) and other arginine metabolites in men after validation of a chromatographic method," Clin Chim Acta. 384:141-148 (2007).
Meyer et al., "High-performance liquid chromatographic determination of nitric oxide synthase-related arginine derivatives in vitro and in vivo," Anal Biochem. 247:11-16 (1997).
Mueller et al., "Long-term stability of endogenous B-type natriuretic peptide (BNP) and amino terminal proBNP (NT-proBNP) in frozen plasma samples," Clin Chem Lab Med. 42(8):942-944 (2004).
Needleman et al., "A general method applicable to the search for similarities in the amino acid sequence of two proteins," J Mol Biol. 48:443-453 (1970).
Nolan et al., "Suspension array technology: evolution of the flat-array paradigm," Trends Biotechnol. 20(1):9-12 (2002).
Pearson et al., "Improved tools for biological sequence comparison," Proc Natl Acad Sci USA. 85:2444-2448 (1988).
Schnabel et al., "Asymmetric dimethylarginine and the risk of cardiovascular events and death in patients with coronary artery disease: results from the AtheroGene Study," Circ Res. 97(5):e53-e59 (2005).
Smith et al., "Comparison of biosequences," Adv Appl Math. 2:482-489 (1981).
Smith et al., "Delayed metabolism of human brain natriuretic peptide reflects resistance to neutral endopeptidase," J Endocrinol. 167:239-246 (2000).
Thompson et al., "The physiological structure of human C-reactive protein and its complex with phosphocholine," Structure. 7(2):169-177 (1999).
Uhlar et al., "Serum amyloid A, the major vertebrate acute-phase reactant," Eur J Biochem. 265:501-523 (1999).
Valtonen et al., "Serum L-homoarginine concentration is elevated during normal pregnancy and is related to flow-mediated vasodilatation," Circ J. 72:1879-1884 (2008).
Wu et al., "Analytical and clinical evaluation of the Bayer ADVIA Centaur automated B-type natriuretic peptide assay in patients with heart failure: a multisite study," Clin Chem. 50(5):867-873 (2004).
Yang et al., "Endothelial arginase: a new target in atherosclerosis," Curr Hypertens Rep. 8:54-59 (2006).
Yeo et al., "Multicenter evaluation of the Roche NT-proBNP assay and comparison to the Biosite Triage BNP assay," Clin Chim Acta. 338:107-115 (2003).
International Search Report for International Application No. PCT/EP2011/051957, mailed May 25, 2011 (4 pages).

* cited by examiner

HOMOARGININE AS A BIOMARKER FOR THE RISK OF MORTALITY

CROSS-REFERENCE TO RELATED APPLICATIONS

This Application is the U.S. National Stage of PCT/EP2011/051957, filed Feb. 10, 2011, which, in turn, claims benefit of European Patent Application No. 10 153 545.8, filed Feb. 12, 2010.

The present invention relates to the field of laboratory diagnostics. Specifically, means and methods for determining the risk of mortality in a patient based on homoarginine and to reduce the risk of mortality by administration of homoarginine are disclosed. Moreover, the present invention relates to the use of homoarginine for the preparation of a medicament for the treatment of a patient having an increased risk of mortality caused by stroke or a cardiac cause. Furthermore, the present application relates to a pharmaceutical composition comprising homoarginine and a composition for foodstuff supplements comprising homoarginine.

An aim of modern medicine is to provide personalized or individualized treatment regimens. Those are treatment regimens which take into account a patient's individual needs or risks. Individualized treatment regimens offer benefits for the individual patient as well as for society as a whole. For the individual patient personalized treatment avoids excessive therapy while ensuring that necessary measures are taken. As every therapy may cause undesired harmful side effects, the avoidance of unnecessary therapies saves the patient from potentially harmful side effects. On the other hand, the identification of patients with special needs ensures that these individuals receive the appropriate treatment. For the health system as a whole the avoidance of unnecessary therapies allows for a more economic use of resources.

Individualized treatment regimens require appropriate diagnostic tools in order to separate those patients who benefit from certain therapeutic measures from the patients who do not. Therefore, the development of individualized treatment regimens critically depends on the development of novel diagnostic tools and procedures. Because the prevention of future disease is often more effective than the therapy of already existing disease, diagnostic tools and methods for risk stratification with respect to future diseases are especially desirable. Cardiovascular diseases are amongst the major causes of death in industrialized countries. Mortality from cardiovascular diseases substantially declined in Westernized countries during the past five decades (Ford, E S et al., 2007, N. Engl. J. Med. 356: 2388-2398). However, despite highly effective measures to control conventional risk factors the incidence of cardiovascular events remains high. This highlights the need to identify independent non-conventional risk factors for acute cardiovascular events such as myocardial infarction, unstable angina pectoris, and stroke.

Homoarginine is a cationic amino acid, which is derived from lysine. Homoarginine increases the availability of NO (Bauersachs, J and Widder, J D, 2008, Pharmacol. Rep. 60: 119126; Chen, P Y and Sanders, P W, 1993, Hypertension 22: 812-818) by two ways; first, homoarginine itself serves as a precursor of NO. Second, it increases the intracellular concentration of L-arginine, the main substrate for NO synthase by inhibiting the enzyme arginase, which competes with NO synthase for the key substrate L-arginine (Hrabak, A et al., 1994, Biochem. Biophys. Res. Comm. 198: 206-212; Knowles, R G et al., 1989, Proc. Natl. Acad. Sci. USA, 86: 5159-5162; Valtonen, P et al., 2008, Circ. J. 72: 1879-1884; Yang, Z and Ming, X F, 2006, Hypertens. Rep. 8: 54-59). The significance of homoarginine to NO metabolism has not fully been understood, but recent evidence suggests that homoarginine is positively related to endothelial function (Valtonen et al., loc. cit.) Homoarginine may exert further actions that are relevant to cardiovascular health including inhibition of platelet aggregation and stimulation of insulin secretion.

Consequently, the problem underlying the present invention could be viewed as the identification of additional markers that allow for a risk stratification of patients with respect to acute cardiovascular events. The problem is solved by the embodiments of the present invention described in the claims and in the specification below.

The present invention relates to a method for determining the risk of mortality in a patient comprising the steps of
a) determining the amount of homoarginine in a sample of the patient; and
b) comparing the determined amount with a reference amount, whereby the risk of mortality in the patient is predicted.

The method of the present invention is, preferably, an in vitro method. Moreover, it may comprise steps in addition to those explicitly mentioned above. For example, further steps may relate to sample pre-treatments or evaluation of the results obtained by the method. The method may be carried out manually or assisted by automation. Preferably, step (a) and/or (b) may in total or in part be assisted by automation, e.g., by a suitable robotic and sensory equipment for the determination in step (a) or a computer-implemented comparison in step (b).

The term "determining the risk of mortality" as used herein refers to assessing the probability according to which a subject will die within a certain time window, i.e. the predictive window. In accordance with the present invention, the predictive window, preferably, is within 1 year, 2 years, 4 years, 6 years, 8 years, 10 years or more after determination of the risk of mortality. Most preferably, the predictive window is within 4 years, 5 years or 6 years. However, as will be understood by those skilled in the art, such an assessment is usually not intended to be correct for 100% of the subjects to be investigated. The term, however, requires that prediction can be made for a statistically significant portion of subjects in a proper and correct manner. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the prediction of an increased, normal or decreased risk will be correct for at least 60%, at least 70%, at least 80%, or at least 90% of the subjects of a given cohort or population. The term, preferably, relates to determining whether or not there is an increased risk of mortality compared to the average risk of mortality in a population of subjects rather than giving a precise probability for the said risk.

The term "patient", preferably, refers to a mammal, more preferably to a human. In a preferred embodiment of the present invention, the patient is healthy with respect to diseases that increase the risk of death from cardiac causes. Said diseases are, preferably, hypertension, renal failure, type 1 diabetes, type 2 diabetes and cardiovascular diseases such as e.g. stroke. In a further preferred embodiment of the present invention the patient suffers from chronic or acute cardiovascular diseases including acute coronary syndromes. In yet another preferred embodiment of the present invention the patient suffers from renal failure requiring haemodialysis and type 2 diabetes.

The term "acute coronary syndrome" refers to myocardial infarction or unstable angina pectoris. Myocardial infarction results from prolonged ischemia of the myocardium due to insufficient blood supply. Prolonged ischemia induces necrosis of the affected areas of the myocardium and, thus, causes damage to the myocardium. Angina pectoris is caused by transient ischemia of the myocardium. Its main symptom is chest pain. Unstable Angina pectoris (as opposed to stable Angina pectoris) occurs at rest, is severe and of recent onset or increases in severity.

The term "sample" refers to a sample of a body fluid, to a sample of separated cells or to a sample from a tissue or an organ. Samples of body fluids can be obtained by well known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which produce the marker referred to herein.

The term "homoarginine" refers to a chemical compound which is described in formula (I) below. Homoarginine is, preferably, L-homoarginine.

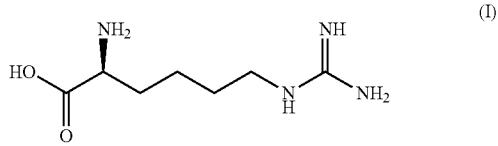 [SMILES: N=C(N)NCCCC[C@H](N)C(=O)O]

(I)

Determining the amount of homoarginine relates to measuring the amount or concentration, preferably semi-quantitatively or quantitatively. Measuring can be done directly or indirectly. Direct measuring relates to measuring the amount or concentration of homoarginine based on a signal which is obtained from the amino acid itself and the intensity of which directly correlates with the number of molecules of the amino acid present in the sample. Such a signal—sometimes referred to herein as intensity signal—may be obtained, e.g., by measuring an intensity value of a specific physical or chemical property of the amino acid. Indirect measuring includes measuring of a signal obtained from a secondary component (i.e. a component not being the amino acid itself) or a biological read out system, e.g., measurable cellular responses, ligands, labels, or enzymatic reaction products. Furthermore, the use of immunoassays for the determination of the marker of the present invention is preferred.

In accordance with the present invention, determining the amount of homoarginine can be achieved by all known means for determining the amount of an amino acid in a sample. Said means, preferably, comprise chromatographic methods detections or methods based on the formation of coloured reaction products.

Especially preferred is the use of chromatographic methods for determining the amount of homoarginine. Most preferred are high performance liquid chromatography (HPLC) and gas chromatography (GC). Gas chromatography and liquid chromatography are, preferably, coupled to mass spectrometry (GC-MS, HPLC-MS) for the identification of the amino acid. These methods are well known to the person skilled in the art. Moreover, most preferably used for determining the amount of homoarginine is high performance liquid chromatography (HPLC) coupled with fluorescence detection, whereby homoarginine and an internal standard from the biological sample are extracted via ion-exchange-solid phase extraction (SPE). Subsequently, the extract is converted into a fluorescent derivative using the reagents ortho-phthalaldehyde and mercaptan (e.g. 2-Mercaptoethanol, 3-Mercaptopropionic acid). The fluorescent derivatives are separated via HPLC and quantitatively determined using fluorescence detection (Meyer, J et al, 1997, Anal Biochem, 247:11-6). The person skilled in the art is well aware of various modifications of this method (WO 2006/128419).

Further preferred chromatographic separation methods for determining the amount of homoarginine include capillary electrophoresis coupled with fluorescence detection, gas chromatography tandem mass spectrometry subsequently after extraction and derivatization (as methylester tri(N-pentafluoropropionyl) derivative), or liquid chromatography-tandem mass spectrometry (HPLC-MS/MS) involving the use of two mass spectrometers, in tandem, as the detector for an HPLC.

Also preferably, determining the amount of homoarginine comprises the step of measuring a specific intensity signal obtainable from homoarginine in the sample.

Determining the amount of homoarginine, preferably, comprises the steps of (a) contacting homoarginine with a specific ligand, (b) optionally removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to homoarginine. Preferred ligands include antibodies, nucleic acids, peptides or polypeptides such as receptors or binding partners for homoarginine and fragments thereof comprising the binding domains for homoarginine. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)$_2$ fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to homoarginine. Specific binding according to the present invention means that the ligand or agent should not bind substantially to ("cross-react" with) another amino acid, peptide, polypeptide or substance present in the sample to be analyzed. Preferably, the specifically bound homoarginine should be bound with at least 3 times higher, more preferably at least 10 times higher and even more preferably at least 50 times higher affinity than any other relevant substance. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantitative. Suitable methods are described in the following.

First, binding of a ligand may be measured directly, e.g. by NMR or surface plasmon resonance.

Second, the ligand may exhibit enzymatic properties itself and the "ligand/peptide or polypeptide" complex or the ligand which was bound to homoarginine, respectively, may be contacted with a suitable substrate allowing detection by the generation of an intensity signal. For measurement of enzymatic reaction products, preferably the amount of substrate is saturating. The substrate may also be labelled with a detectable label prior to the reaction. Preferably, the sample is contacted with the substrate for an adequate period of time. An adequate period of time refers to the time necessary for a detectable, preferably measurable, amount of product to be produced. Instead of measuring the amount of product, the time necessary for appearance of a given (e.g. detectable) amount of product can be measured.

Third, the ligand may be coupled covalently or non-covalently to a label allowing detection and measurement of the ligand. Labelling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include $^{35}$S, $^{125}$I, $^{32}$P, $^{33}$P and the like. A radioactive label can be detected by any method known and appropriate, e.g. a light-sensitive film or a phosphor imager. Suitable measurement methods according to the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labelling or other detection methods as described above.

The amount of homoarginine may be, also preferably, determined as follows: (a) contacting a solid support comprising a ligand for the homoarginine as specified above with a sample comprising homoarginine and (b) measuring the amount of homoarginine which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention [Nolan 2002, Trends Biotechnol. 20(1):9-12]. In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

The term "comparing" as used herein encompasses comparing the amount of homoarginine comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e. automatically provide the desired assessment in a suitable output format. Based on the comparison of the amounts determined in step a) and the reference amount of the method of the present invention, it is possible to predict the risk of the subject of suffering of one or more of the complications referred to herein. Therefore, the reference amount is to be chosen so that either a difference or a similarity in the compared amounts allows identifying those patients whose risk of mortality is increased.

Accordingly, the term "reference amount" as used herein refers to an amount which allows determining whether a patient has an increased risk of mortality. Accordingly, the reference may be (i) derived from a patient known to be at increased risk of mortality or (ii) it may be derived from a patient known not to be at increased risk of mortality. Preferably, the reference amount is determined on the basis of an averaged median amount obtained from a group of patients meeting the criteria either of (i) or of (ii), described above. Moreover, the reference amount may define a threshold amount, whereby an amount smaller than the threshold shall be indicative for a subject which is at increased risk of mortality. The reference amount applicable for an individual subject may vary depending on various physiological parameters such as age, gender, or subpopulation, as well as on the means used for the determination of the amino acid referred to herein. A suitable reference amount may be determined by the method of the present invention from a reference sample to be analyzed together, i.e. simultaneously or subsequently, with the test sample. A preferred reference amount serving as a threshold may be derived from the lower limit of normal (LLN), i.e. the lower limit of the physiological amount to be found in samples from a population of subjects not being at increased risk of mortality. The LLN for a given population of subjects can be determined by various well known techniques. A suitable technique may be to determine the median or average of the population for the amino acid amounts to be determined in the method of the present invention.

Preferably, an amount of homoarginine above about 1.40 μM indicates a low risk of mortality while an amount of homoarginine below this level indicates an increased risk of mortality. An amount of homoarginine below about 1.10 μM, preferably, indicates an increased risk of mortality.

The term "about" is meant to indicate +/−30% of the indicated amount, preferably +/−20% of the indicated amount, more preferably +/−10% of the indicated amount, most preferably +/−5% of the indicated amount.

Advantageously, the present invention provides a reliable biomarker for determining the risk of mortality. The identification of high risk patients allows for a closer monitoring of this group so that preventive treatments can be administered to those patients with the greatest need. Moreover, homoarginine increases the availability of nitric oxide and is probably positively related to endothelial function. This fact taken together with the finding of the study underlying the present invention that low amounts of homoarginine correlate with increased mortality, moreover, suggests specific preventive measures: patients with low amounts of homoarginine should receive therapies that aim at increasing homoarginine and/or NO-levels and at supporting endothelial function. Another finding of the study is the association of homoarginine status and stroke risk, whereby low serum homoarginine levels are identified as a novel risk factor for strokes. Thus, the present invention contributes to the development of individualized treatment regimens.

It is to be understood that the definitions and explanations of the methods, measurements, and terms made above apply mutatis mutandis for all aspects described in this specification in the following except as otherwise indicated.

Moreover, the method of the present invention, preferably, further comprises the steps of c) determining the amount of the following marker selected from the group consisting of: TnT, NT-proBNP, BNP, ANP, CRP, SAA, Neopterin, ADMA, and/or SDMA in said sample simultaneously to the amount of homoarginine in step a), d) comparing the amount of the marker determined in step c) with a reference amount, whereby the risk of mortality in the patient is determined.

The present invention takes advantage of further certain markers. The term "marker" is known to the person skilled in the art. In particular, markers are gene expression products which are differentially expressed, i.e. up regulated or down regulated in presence or absence of a certain condition, disease, or complication. Usually, a marker is defined as a nucleic acid (including mRNA), a protein, peptide, or small molecule compound. The amount of a suitable marker can indicate the presence or absence of the condition, disease, or complication, and thus allow diagnosis. Preferably, said marker are selected from the group consisting of TnT, NT-proBNP, BNP, ANP, CRP, SAA, Neopterin, ADMA, and/or SDMA The term "cardiac Troponin (TnT)" as used herein refers to all Troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493. Preferably, cardiac Troponin refers to Troponin T and/or Troponin I, and, most preferably, to Troponin T. It is to be understood that isoforms of Troponins may be determined in the method of the present invention together, i.e. simultaneously or sequentially, or individually, i.e. without determining the other isoform at all. Amino acid sequences for human Troponin T and human Troponin I are disclosed in Anderson, loc cit and Ferrieres 1998, Clinical Chemistry, 44: 487-493. The term "cardiac Troponin" encompasses also variants of the aforementioned specific Troponins, i.e., preferably, of Troponin I, and more preferably, of Troponin T. Such variants have at least the same essential biological and immunological properties as the specific cardiac Troponins. In particular, they share the same essential biological and immunological properties if they are detectable by the same specific assays referred to in this specification, e.g., by ELISA Assays using polyclonal or monoclonal antibodies specifically recognizing the said cardiac Troponins. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific Troponin. Variants may be allelic variants or any other species specific homologs, paralogs, or orthologs. Moreover, the variants referred to herein include fragments of the specific cardiac Troponins or the aforementioned types of variants as long as these fragments have the essential immunological and biological properties as referred to above. Such fragments may be, e.g., degradation products of the Troponins. Further included are variants which differ due to posttranslational modifications such as phosphorylation or myristylation.

The terms "Atrial Natriuretic Peptide (ANP)" and "Brain Natriuretic Peptide (BNP)" as used herein comprise ANP-type and BNP-type peptides and variants thereof (Bonow 1996, Circulation 93, 1946). ANP-type peptides comprise pre-proANP, proANP, NT-proANP, and ANP. BNP-type peptides comprise pre-proBNP, proBNP, NT-proBNP, and BNP. The pre-pro peptide (134 amino acids in the case of pre-proBNP) comprises a short signal peptide, which is enzymatically cleaved releasing the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP). Preferably, natriuretic peptides according to the present invention are NT-proANP, ANP, and, more preferably, NT-proBNP, BNP, and variants thereof. ANP and BNP are the active hormones and have a shorter half-life than their respective inactive counterparts, NT-proANP and NT-proBNP. BNP is metabolised in the blood, whereas NT-proBNP circulates in the blood as an intact molecule and as such is eliminated renally. The in-vivo half-life of NTproBNP is 120 min longer than that of BNP, which is 20 min (Smith 2000, J Endocrinol 167, 239). Preanalytics are more robust with NT-proBNP allowing easy transportation of the sample to a central laboratory (Mueller 2004, Clin Chem Lab Med 42, 942). Blood samples can be stored at room temperature for several days or may be mailed or shipped without recovery loss. In contrast, storage of BNP for 48 hours at room temperature or at 40 Celsius leads to a concentration loss of at least 20% (Wu 2004, Clin Chem 50, 867). Therefore, depending on the time-course or properties of interest, either measurement of the active or the inactive forms of the natriuretic peptide can be advantageous. The most preferred natriuretic peptides according to the present invention are NT-proBNP or variants thereof. The human NT-proBNP, as referred to in accordance with the present invention, is a polypeptide comprising, preferably, 76 amino acids in length corresponding to the N-terminal portion of the human NT-proBNP molecule. The structure of the human BNP and NT-proBNP has been described already in detail in the prior art (WO 02/089657, WO 02/083913, or Bonow 1996, Circulation 93, 1946). Preferably, human NT-proBNP as used herein is human NT-proBNP as disclosed in EP 0648228 B1. These prior art documents are herewith incorporated by reference with respect to the specific sequences of NT-proBNP and variants thereof disclosed therein. The NT-proBNP referred to in accordance with the present invention further encompasses allelic and other variants of said specific sequence for human NT-proBNP discussed above. Specifically, envisaged are variant polypeptides which are on the amino acid level preferably, at least 50%, 60%, 70%, 80%, 85%, 90%, 92%, 95%, 97%, 98%, or 99% identical, to human NT-proBNP. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm (Smith and Waterman 1981, Add APL Math 2, 482), by the homology alignment algorithm (Needleman and Wunsch 1970, J Mol Biol 48, 443), by the search for similarity method (Pearson and Lipman 1988, Proc Natl Acad Sci 85, 2444), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the said polypeptides have NT-proBNP properties. NT-proBNP properties as referred to herein are immunological and/or biological properties. Preferably, the NT-proBNP variants have immunological properties (i.e. epitope composition) comparable to those of NT-proBNP. Thus, the variants shall be recognizable by the aforementioned means or ligands used for determination of the amount of the natriuretic peptides. Biological and/or immunological NT-proBNP properties can be detected by the assay described in (Karl 1999, Scand J Clin Invest 230,177; Yeo 2003, Clinica Chimica Acta 338, 107). Variants also include posttranslationally modified peptides such as glycosylated peptides. Further, a variant in accordance with the present invention is also a peptide or polypeptide which has been modified after collection of the sample, for example by covalent or non-covalent attachment of a label, particularly a radioactive or fluorescent label, to the peptide. Examples of variants are known. E.g. variants of NT-proANP and NT-proBNP and methods for their measurement have been described (Ala-Kopsala 2004, Clin Chem 50, 1576). Molecular heterogeneity has a major impact on the measurement of circulating N-terminal fragments of A-type and B-type natriuretic peptides.

The term "C-reactive protein (CRP)" as used herein refers to the 224-amino acid residue protein with a monomer molar mass of 25106 Da having a shape of an annular pentameric disc (Thompson, D et al, 1999, Structure 7, 169-177). Moreover, CRP is a member of the small pentraxins family.

The term "human serum amyloid A (SAA)" as used herein, relates to a mature SAA protein including human SAA1 (A-SAA), SAA2 (A-SAA), or SAA4 (C-SAA) ranging in size from 104 to 112 amino acids derived from primary translation products with 18-amino acid leader peptides (Uhlar, C. M., et al, 1999, Eur. J. Biochem. 265, 501-523). SAAs are predominantly produced by the liver and belonging to a family of apolipoproteins associated with high-density lipoprotein (HDL) in plasma. Different isoforms of SAA are expressed constitutively (constitutive SAAs (C-SAA)) at different levels or in response to inflammatory stimuli (acute phase SAAs (A-SAA)).

The term "Neopterin" as used herein refers to 2-amino-6-(1,2,3-trihydroxypropyl)-1H-pteridin-4-one and is a catabolic product of guanosine triphosphate (GTP), a purine nucleotide.

Furthermore, the term "asymmetric dimethyl arginine (ADMA) as used herein refers to N',N'-Dimethylarginine, or (2S)-2-Amino-5-[(amino-dimethylaminomethylene) amino]-pentanoic acid and the term "symmetric dimethyl-arginine (SDMA) as used herein refers to N',N"-Dimethyl-arginine an isomer of ADMA.

In a preferred embodiment of the method of the present invention, dependent on the respective above described further marker an amount of said marker different from the respective reference amount indicates an increased or decreased risk of mortality determined in step d.

In a preferred embodiment of the present invention the risk mortality to be determined according to the method of the present invention is due to cardiovascular mortality. Cardiovascular mortality refers to all cases of death that are related to cardiovascular causes. Preferably, these cardiovascular causes are myocardial infarction, death from congestive heart failure, death from stroke, death following coronary artery bypass graft surgery and death following percutaneous coronary intervention.

It is to be understood that according to the method of the present invention the risk of a patient of suffering from non-lethal adverse cardiovascular events can be determined. Because not every adverse cardiovascular event is lethal, an increased risk of death from cardiac causes in patients with low homoarginine levels indicates an increased general risk of non-lethal adverse cardiovascular events as well.

The term "coronary artery disease" or "CAD" refers to a condition also known as atherosclerotic heart disease. This condition is characterized by the accumulation of atherosclerotic plaque at the walls of the coronary arteries. Once the accumulation exceeds a certain level, the blood flow through the artery is impaired. This condition causes Angina pectoris and may cause myocardial infarction, especially if the plaque ruptures. Common intervention to treat CAD comprises percutaneous coronary intervention (PCI) and coronary artery bypass graft surgery.

In a further preferred embodiment of the present invention mortality is due to a wasting disease or a chronic consuming disease. The term "wasting disease" refers to every disease which induces the loss of muscles and/or fat. Said loss may be localized to certain organs or body parts or generalized. Preferably, the term "wasting disease" refers to cancer, tuberculosis, and other chronic infectious disease or malnutrition.

Moreover, the present invention relates to a method for deciding whether a patient is in need of the administration of homoarginine comprising the steps of
a) determining the amount of homoarginine in a sample of the patient;
b) comparing the determined amount with a reference amount, whereby it is decided whether the patient requires administration of homoarginine.

The link between low amounts of homoarginine and an increased risk of mortality discovered in the study underlying the present invention allows for the identification of those patients whose increased risk of mortality is due to a lack of homoarginine. Hence, these patients should receive additional homoarginine to decrease said risk.

Another preferred embodiment of the present invention relates to the use of homoarginine for the determination of the risk of mortality in a patient.

Yet another embodiment of the present invention relates to a device for predicting the risk of mortality in a patient comprising
a) an analyzing unit for determining the amount of homoarginine in a sample of the patient; and
b) an evaluation unit for comparing the determined amount with a suitable reference amount and for predicting the risk of mortality of the patient.

The term "device" as used herein relates to a system of means comprising at least the aforementioned means operatively linked to each other as to practise the method of the present invention. Preferred means for determining the amounts of the markers of the present invention, and means for carrying out the comparison are disclosed above in connection with the method of the invention. How to link the means in an operating manner will depend on the type of means being included into the device. For example, where an analysis unit for automatically determining the amount of the amino acid of the present invention is applied, the data obtained by said automatically operating analysis unit can be processed by, e.g., a computer as evaluation unit in order to obtain the desired results. Preferably, the means are comprised in a single device in such a case.

Said device, preferably, includes an analyzing unit for the measurement of the amount of homoarginine in an applied sample and an evaluation unit for processing the resulting data. Preferably, the evaluation unit comprises a database with the stored reference amounts and a computer program code which when tangibly embedded on a computer carries out the comparison of the determined amounts and the reference amounts stored in the database. More preferably, the evaluation unit comprises a further computer program code which allocates the result of the comparison to a risk prediction. In such a case, it is, also preferably, envisaged that the evaluation unit comprises a further database wherein the reference amounts are allocated to the risks.

Alternatively, where means such as test stripes are used for determining the amount of homoarginine, the evaluation unit may comprise control stripes or tables allocating the determined amount to a reference amount. The test stripes are, preferably, coupled to ligands which specifically bind to homoarginine. The strip or device, preferably, comprises means for detection of the binding of said homoarginine to said ligands. Preferred means for detection are disclosed in connection with embodiments relating to the method of the invention above. In such a case, the analysis unit and the evaluation unit are operatively linked in that the user of the system brings together the result of the determination of the amount and the diagnostic or prognostic value thereof due to the instructions and interpretations given in a manual. The analysis unit and the evaluation unit may appear as separate devices in such an embodiment and are, preferably, packaged together as a kit. The person skilled in the art will realize how to link the means without further ado. Preferred devices are those which can be applied without the particular knowledge of a specialized clinician, e.g., test stripes or electronic devices which merely require loading with a sample. The results may be given as output of raw data which need interpretation by the clinician. Preferably, the output of the device is, however, processed, i.e. evaluated, raw data the interpretation of which does not require a clinician. Further preferred devices comprise the analyzing units/devices (e.g., biosensors, arrays, solid supports coupled to ligands specifically recognizing homoarginine, Plasmon surface resonance devices, NMR spectrometers, mass-spectrometers etc.) or evaluation units/devices referred to above in accordance with the method of the invention.

Another preferred embodiment of the present invention relates to a kit for predicting the risk of mortality in a patient comprising
a) an analyzing agent for determining the amount of homoarginine in a sample of the patient; and
b) an evaluation unit for comparing the amount determined by the analyzing agent with a suitable reference amount, said unit further allowing the prediction of the risk of the patient to suffer from mortality.

The term "kit" as used herein refers to a collection of the aforementioned components of which may or may not be packaged together. The components of the kit may be comprised by separate vials (i.e. as a kit of separate parts) or provided in a single vial. Moreover, it is to be understood that the kit of the present invention is to be used for practising the methods referred to herein above. It is, preferably, envisaged that all components are provided in a ready-to-use manner for practising the methods referred to above. Further, the kit preferably contains instructions for carrying out the said methods. The instructions can be provided by a user's manual in paper- or electronic form. For example, the manual may comprise instructions for interpreting the results obtained when carrying out the aforementioned methods using the kit of the present invention. The kit shall comprise an analyzing agent. This agent is capable of specifically recognizing homoarginine in a sample of the subject. Moreover, the said agent(s) shall upon binding to homoarginine, preferably, be capable of generating a detectable signal, the intensity of which correlates to the amount of homoarginine present in the sample. Dependent on the type of signal which is generated, methods for detection of the signal can be applied which are well known in the art. Analyzing agents which are preferably used for the kit of the present invention include antibodies or aptamers. The analyzing agent may be present on a test stripe as described elsewhere herein. The amount homoarginine thus detected can than be further evaluated in the evaluation unit. Preferred evaluation units to be used for the kit of the present invention include those referred to elsewhere herein.

It is to be understood that the definitions and explanations of the methods, measurements, and terms made above apply mutatis mutandis for all aspects described in this specification in the following except as otherwise indicated.

In an embodiment the invention relates to a method for determining the risk of mortality in a patient comprising the steps of
a) determining the amount of homoarginine or its metabolic precursors in a sample of the patient; and
b) comparing the determined amount with a reference amount, whereby the risk of mortality in the patient is predicted.

In another embodiment the invention relates to a method for deciding whether a patient is in need of the administration of homoarginine comprising the steps of
a) determining the amount of homoarginine or its metabolic precursor in a sample of the patient;
b) comparing the determined amount with a reference amount, whereby it is decided whether the patient requires administration of homoarginine.

In a further preferred embodiment the present invention relates to the use of homoarginine or its metabolic precursors for the determination of the risk of mortality in a patient.

Yet another embodiment of the present invention relates to a device for predicting the risk of mortality in a patient comprising
a) an analyzing unit for determining the amount of homoarginine or its metabolic precursors in a sample of the patient; and
b) an evaluation unit for comparing the determined amount with a suitable reference amount and for predicting the risk of mortality of the patient.

Another preferred embodiment of the present invention relates to a kit for predicting the risk of mortality in a patient comprising
a) an analyzing agent for determining the amount of homoarginine or its metabolic precursors in a sample of the patient; and
b) an evaluation unit for comparing the amount determined by the analyzing agent with a suitable reference amount, said unit further allowing the prediction of the risk of the patient to suffer from mortality.

In a preferred embodiment of the invention the aforementioned metabolic precursor is lysine.

Lysine is an α-amino acid with the chemical formula $HO_2CCH(NH_2)(CH_2)_4NH_2$. It is an essential amino acid, as it is not synthesized in animals, hence it must be ingested as lysine or lysine-containing proteins. In plants and bacteria, it is synthesized from aspartic acid (aspartate). Lysine is a base. The ε-amino group often participates in hydrogen bonding and as a general base in catalysis. Common post-translational modifications include methylation of the ε-amino group, giving methyl-, dimethyl-, and trimethyllysine. The latter occurs in calmodulin. Other posttranslational modifications at lysine residues include acetylation and ubiquitination. Collagen contains hydroxylysine which is derived from lysine by lysyl hydroxylase. O-Glycosylation of lysine residues in the endoplasmic reticulum or Golgi apparatus is used to mark certain proteins for secretion from the cell. Lysine is metabolised in mammals to give acetyl-CoA, via an initial transamination with a-ketoglutarate. The bacterial degradation of lysine yields cadaverine by decarboxylation. Allysine is a derivative of lysine, used in the production of elastin and collagen. It is produced by the actions of the enzyme lysyl oxidase on lysine in the extracellular matrix and is essential in the crosslink formation that stabilizes collagen and elastin. L-Lysine is a necessary building block for all proteins in the body. L-Lysine plays a major role in calcium absorption; building muscle protein; recovering from surgery or sports injuries; the body's production of hormones, enzymes, and antibodies. Lysine can be modified through acetylation, methylation, ubiquitination, sumoylation, neddylation, biotinylation, and carboxylation which tends to modify the function of the protein of which the modified lysine residue(s) are a part.

Furthermore, the present invention relates to the use of homoarginine for the preparation of a medicament for the treatment of a patient having an increased risk of mortality caused by stroke or a cardiac cause.

Moreover, the present invention relates to a pharmaceutical composition comprising homoarginine.

The term "medicament" as used herein refers, in one aspect, to a pharmaceutical composition containing homoarginine as pharmaceutical active compound, wherein the pharmaceutical composition may be used for human or non human therapy of various diseases or disorders in a therapeutically effective dose.

The pharmaceutical compositions and formulations referred to herein are administered at least once in order to treat or ameliorate or prevent a disease or condition recited in this specification. However, the said pharmaceutical compositions may be administered more than one time.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent. The resulting formulations are to be adapted to the mode of administration. Dosage recommendations shall be indicated in the prescribers or users instructions in order to anticipate dose adjustments depending on the considered recipient.

A pharmaceutical composition as used herein comprises homoarginine, and preferably, one or more pharmaceutically acceptable carrier.

The pharmaceutical composition is, preferably, administered in conventional dosage forms prepared by combining the drugs with standard pharmaceutical carrier according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active compound with which it is to be combined, the route of administration and other well-known variables. However, depending on the nature and the mode of action of an active compound the pharmaceutical composition may be administered by other routes as well.

The carrier(s) must be acceptable in the sense of being compatible with the other ingredients of the formulation and being not deleterious to the recipient thereof. The pharmaceutical carrier employed may be, for example, a solid, a gel or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl monostearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or non-toxic, non-therapeutic, non-immunogenic stabilizers and the like.

A therapeutically effective dose refers to an amount of the pharmaceutically active compound to be used in a pharmaceutical composition of the present invention which prevents, ameliorates or treats the symptoms accompanying a disease or condition referred to in this specification. Therapeutic efficacy and toxicity of the compound can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

The medicament according to the present invention may, preferably, comprise drugs in addition to homoarginine which are added to the pharmaceutical composition during its formulation. Finally, it is to be understood that the formulation of a pharmaceutical composition takes place under GMP standardized conditions or the like in order to ensure quality, pharmaceutical security, and effectiveness of the medicament.

The term "composition" refers to any composition formulated in solid, liquid (or gaseous) form. Said composition comprises homoarginine optionally together with suitable auxiliary compounds such as diluents or carriers or further ingredients. In this context, it is distinguished for the present invention between auxiliary compounds, i.e. compounds which do not contribute to the effects elicited by the compound of the present invention upon application of the composition for its desired purpose, and further ingredients, i.e. compounds which contribute a further effect or modulate the effect of the compound of the present invention. Suitable diluents and/or carriers depend on the purpose for which the composition is to be used and the other ingredients. The person skilled in the art can determine such suitable diluents and/or carriers without further ado. Examples of suitable carriers and/or diluents are disclosed elsewhere herein. Compositions suitable for oral administration may be presented as discrete units such as capsules, cachets, tablets, or lozenges, each containing a predetermined amount of homoarginine described herein. Other compositions include suspensions in aqueous liquors or non-aqueous liquids such as a syrup, an elixir, or an emulsion.

In a further aspect of the invention, the aforementioned composition is a medicament as specified elsewhere in the description in more detail. In one aspect the said medicament can be used to reduce the risk of mortality caused by stroke or a cardiac cause.

In another aspect of the invention, the composition is for foodstuff supplements comprising homoarginine which can be formulated in an equivalent manner as described for a pharmaceutical composition above. The composition for foodstuff supplements may comprise additionally food grade components.

As used herein, an effective amount of homoarginine is a dosage large enough to produce the desired therapeutic effect to reduce the risk of mortality. An effective amount is not, however, a dosage so large as to cause adverse side effects. Generally, an effective amount may vary with the patient's age, condition, weight and sex, as well as the extent of the condition being treated, and can be determined by one of skill in the art. The dosage may be adjusted by the individual practitioner in the event of any complication.

All references cited in this specification are herewith incorporated by reference with respect to their entire disclosure content and the disclosure content specifically mentioned in this specification.

The following example is only intended to illustrate the present invention and shall not limit the scope of the invention in any way.

EXAMPLE

Study Design and Participants

The 4D study was a prospective randomized controlled trial including 1255 patients with type 2 diabetes mellitus, age 18-80 years, and treated by hemodialysis for less than 2 years. Between March 1998 and October 2002, patients were recruited in 178 dialysis centres in Germany. Patients were randomly assigned to double-blinded treatment with either 20 mg atorvastatin (n=619) or placebo (n=636) once daily, and were followed-up until the date of death, censoring, or end of the study in March 2004. The primary endpoint of the 4D study was defined as a composite of death from cardiac causes, stroke and myocardial infarction (MI), whichever occurred first. 4D study endpoints were centrally adjudicated by three members of the endpoint committee blinded to study treatment and according to pre-defined criteria. In both studies, cardiovascular deaths included sudden cardiac death, fatal myocardial infarction, death due to congestive heart failure, death after intervention to treat CAD, other deaths due to cardiac causes and fatal stroke.

Data Collection

Information on age, gender and smoking status was obtained through patient interviews. Smoking status was classified as never, former or current. Comorbidities were reported by the patients' treating physicians. Blood pressure was measured in sitting position. Hypertension was diagnosed if the systolic and/or diastolic blood pressure exceeded 140 and/or 90 mmHg or if there was a history of hypertension, evident through the use of antihypertensive drugs.

Blood samples were taken before the start of dialysis in 4D patients. Homoarginine was uniformly measured with a reverse-phase HPLC method in serum stored at −80° C. Within-day coefficients of variation (CV) were 4.7% (1.21 µM) and 2.2% (3.53 µM), and between-day CV were 7.9% (1.25 µM) and 6.8% (3.66 µM), respectively. C-reactive protein was measured with a high sensitivity immunonephelometry (Dade Behring Marburg, Germany).

Statistical Analysis

Continuous variables were expressed as mean with standard deviation or median with interquartile range (IQR) as appropriate, and categorical variables were expressed as percentages.

The association of homoarginine with cardiovascular and all-cause death was calculated using homoarginine as continuous variable (logarithmically transformed), and as categorical variable according to quartiles. Absolute (incidence) rates, and relative risks derived from Cox regression analyses were calculated. Multivariable adjustments were made as described in the legend to table 2. Pearson correlation coefficients were assessed. Additional linear regression analyses were adjusted for common cardiovascular risk factors including blood pressure, smoking, body mass index and cholesterol levels.

All p-values are reported two-sided. Analyses were performed using SPSS version 16.0.

TABLE 1

Baseline characteristics of individuals participating in the 4D study (type 2 diabetics on haemodialysis)

| | |
|---|---|
| Age [years] | 65.7 (8.3) |
| Sex [% male] | 54 |
| Arterial hypertension [%] | 89 |
| Systolic blood pressure [mmHg] | 146 (22) |
| Diastolic blood pressure [m Hg] | 76 (11) |
| Smoker/Ex-smoker [%] | 41 |
| Body mass index [kg/m$^2$] | 27.5 (4.8) |
| Coronary artery disease [%] | 29 |
| Congestive heart failure* [%] | 35 |
| Homoarginine [µM] | 1.2 (0.5) |
| LDL cholesterol [mg/dl] | 126 (30) |
| HDL cholesterol [mg/dl] | 36 (13) |
| Albumin [g/dl] | 3.8 (0.3) |
| Haemoglobin [g/dl] | 10.9 (1.3) |
| HbA1c [%] | 6.7 (1.3) |
| C-reactive protein [mg/dl] | 5.0 (2.3-12.4) |

Values are presented as mean (SD) or median (interquartile range) or %
*Congestive heart failure as defined by NYHA II to IV

TABLE 2

Hazard ratios (95% confidence intervals) for all-cause and cardiovascular mortality according to quartiles of serum homoarginine concentrations at baseline in participants in the 4D study

| Model | Quartile | All-cause mortality HR (95% CI) | P | Cardiovasc. mortality HR (95% CI) | P |
|---|---|---|---|---|---|
| Crude | 1 | 2.1 (1.7-2.7) | <0.001 | 2.2 (1.5-3.0) | <0.001 |
| | 2 | 1.9 (1.5-2.4) | <0.001 | 2.2 (1.5-3.0) | <0.001 |
| | 3 | 1.3 (1.0-1.6) | 0.07 | 1.4 (1.0-2.1) | 0.05 |
| | 4 | 1 | | 1 | |
| Adjusted$^1$ | 1 | 2.0 (1.6-2.6) | <0.001 | 2.0 (1.4-2.9) | <0.001 |
| | 2 | 1.8 (1.4-2.3) | <0.001 | 2.1 (1.5-3.0) | <0.001 |
| | 3 | 1.2 (1.0-1.6) | 0.11 | 1.4 (1.0-2.0) | 0.08 |
| | 4 | 1 | | 1 | |
| Adjusted$^2$ | 1 | 1.7 (1.4-2.2) | <0.001 | 1.8 (1.2-2.5) | 0.002 |
| | 2 | 1.7 (1.4-2.2) | <0.001 | 2.0 (1.4-2.8) | <0.001 |
| | 3 | 1.2 (1.0-1.6) | 0.14 | 1.4 (1.0-2.0) | 0.08 |
| | 4 | 1 | | 1 | |

Adjusted$^1$: Adjustments were for age and sex.
Adjusted$^2$: Adjustments were for age, sex, systolic blood pressure, congestive heart failure, smoking status, body mass index, LDL-cholesterol, haemoglobin, albumin, glycated haemoglobin A1c
*Cardiovascular mortality included sudden cardiac death, fatal myocardial infarction, death due to heart failure, death after intervention to treat coronary artery disease, fatal stroke and other deaths due to cardiac causes.

TABLE 3

Results from the 4D study

| | All-cause mortality | Cardiovascular mortality* |
|---|---|---|
| Events | 617 | 310 |
| Person-years | 3558 | 3558 |
| Incidence rate/100 person-years | 17.3 | 8.7 |
| 1$^{st}$ Quartile (<0.87 µM) | 23.4 | 11.2 |
| 2$^{nd}$ Quartile (0.87-1.10 µM) | 20.8 | 11.4 |
| 3$^d$ Quartile (1.10-1.40 µM) | 14.3 | 7.5 |
| 4$^{th}$ Quartile (>1.40 µM) | 11.4 | 5.3 |

*Cardiovascular mortality included sudden cardiac death, fatal myocardial infarction, death due to congestive heart failure, death after intervention to treat coronary artery disease, fatal stroke and other deaths due to cardiac causes.

Results

The baseline characteristics of the patients are shown in Table 1. Homoarginine levels were higher in males than in females, and were lower with increasing age. Low homoarginine levels correlated with low albumin, low body mass index, low LDL cholesterol, presence of congestive heart failure and longer duration of type 2 diabetes mellitus. During a median follow-up of 4 years, 617 patients died, of whom 310 died from cardiovascular causes (see Table 3). Low homoarginine levels were strongly associated with increased mortality: the relative risks of cardiovascular and all-cause death were more than doubled (+120%) per unit decrease in log transformed homoarginine ($HR_{CVdeath}$ 2.2, 95% CI, 1.7-3.0; $HR_{Death}$ 2.2, 95% CI, 1.8-2.7). Accordingly, in patients in the lowest homoarginine quartile (<0.87 μmol/L) mortality was >2 fold higher than in patients in the highest quartile (>1.4 μmol/L). Such strong associations persisted after multivariable adjustments (Table 2).

The invention claimed is:

1. A method for treating a patient having an increased risk of mortality caused by stroke, sudden cardiac death, myocardial infarction, heart failure, or intervention to treat coronary artery disease, the method comprising:

measuring the amount of homoarginine in a blood sample from the patient;

comparing the amount of homoarginine measured from the patient with a reference amount of homoarginine;

determining the patient has an increased risk of mortality when the amount of hormoarginine from the patient is lower than the reference amount, wherein the increased risk of mortality is increased risk of mortality caused by stroke, sudden cardiac death, myocardial infarction, heart failure, or intervention to treat coronary artery disease; and treating the patient determined to be at increased risk of mortality by administering homoarginine to said patient.

2. The method of claim 1, wherein the patient suffers from a condition that increases the risk of adverse cardiovascular outcomes.

3. The method of claim 2, wherein the patient suffers from acute coronary syndromes, type 2 diabetes, or renal failure requiring haemodialysis.

4. The method of claim 1, wherein the patient is determined to be at increased risk of mortality when the amount of homoarginine in the blood sample from the patient is below 1.40 μM.

5. The method of claim 4, wherein the amount of homoarginine in said blood sample is determined by chromatographic methods, by the use of immunoassays, or by methods based on the formation of colored reaction products.

6. The method of claim 5, wherein said chromatographic methods are high pressure chromatography (HPLC) or gas chromatography (GC).

7. The method of claim 5, wherein said chromatographic methods are coupled to mass spectrometry.

* * * * *

UNITED STATES PATENT AND TRADEMARK OFFICE
CERTIFICATE OF CORRECTION

PATENT NO. : 9,506,909 B2
APPLICATION NO. : 13/578527
DATED : November 29, 2016
INVENTOR(S) : Winfried März et al.

It is certified that error appears in the above-identified patent and that said Letters Patent is hereby corrected as shown below:

In the Claims

Column 19, in Claim 1, Line 20, replace "hormoarginine" with --homoarginine--.

Signed and Sealed this
Twenty-first Day of March, 2017

Michelle K. Lee
*Director of the United States Patent and Trademark Office*